(12) United States Patent
Koerdt et al.

(10) Patent No.: US 6,653,841 B1
(45) Date of Patent: Nov. 25, 2003

(54) DEVICE AND METHOD FOR CARRYING OUT A CONTACTLESS MEASUREMENT OF THE CONDUCTIVITY OF A LIQUID SITUATED IN A FLOW CHANNEL

(75) Inventors: Franz-Wilhelm Koerdt, Bad Nauheim (DE); Peter Kaiser, Frankfurt am Main (DE); Hans Georg Hülsmann, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/463,683
(22) PCT Filed: May 18, 1999
(86) PCT No.: PCT/DE99/01492
§ 371 (c)(1), (2), (4) Date: Jun. 28, 2000
(87) PCT Pub. No.: WO99/61900
PCT Pub. Date: Dec. 2, 1999

(30) Foreign Application Priority Data

May 28, 1998 (DE) .......................... 198 23 836

(51) Int. Cl.[7] .............................................. G01R 27/02
(52) U.S. Cl. ...................... 324/445; 324/655; 324/668
(58) Field of Search ................ 324/204, 207, 324/243, 671, 439, 446, 449, 655, 668, 657, 681, 682; 73/61.43, 61.61; 328/155, 262

(56) References Cited

U.S. PATENT DOCUMENTS

| | | | | |
|---|---|---|---|---|
| 3,404,335 A | | 10/1968 | Kidder | ...................... 379/323 |
| 3,686,926 A | * | 8/1972 | Miller | ........................ 324/693 |
| 4,644,285 A | * | 2/1987 | Britton | ....................... 324/425 |
| 4,682,105 A | * | 7/1987 | Thorn | ........................ 324/671 |
| 5,059,902 A | * | 10/1991 | Linder | ........................ 324/765 |
| 5,077,525 A | * | 12/1991 | West | |
| 5,089,776 A | * | 2/1992 | Furukawa | .................... 324/242 |
| 5,130,639 A | * | 7/1992 | Hachey | |
| 5,157,332 A | * | 10/1992 | Reese | |
| 5,225,783 A | * | 7/1993 | Suzuki | ....................... 324/655 |
| 5,334,932 A | * | 8/1994 | Nielsen | ...................... 324/207 |
| 5,414,368 A | * | 5/1995 | Ogawa | ........................ 324/675 |
| 5,480,511 A | * | 1/1996 | Barbee | |
| 5,485,083 A | * | 1/1996 | Pulice | ........................ 324/204 |

FOREIGN PATENT DOCUMENTS

| | | |
|---|---|---|
| CH | 419 670 | 3/1967 |
| DE | 860 663 | 12/1952 |
| DE | 12 81 567 | 10/1968 |
| DE | 28 22 943 | 11/1979 |
| DE | 37 18 111 | 12/1987 |
| EP | 0 603 020 | 6/1994 |

* cited by examiner

*Primary Examiner*—Kamand Cuneo
*Assistant Examiner*—Trung Nguyen
(74) *Attorney, Agent, or Firm*—Kenyon & Kenyon

(57) ABSTRACT

The invention relates to a device and method for carrying out a contactless measurement of the conductivity of a liquid situated in a flow channel, and to the use of said device and method. According to the invention, the invention provides that a toroidal coil is precisely arranged around the flow channel. Said toroidal coil is interconnected with a capacitor to an oscillating circuit. The invention also provides that the electric characteristics of this circuit are then measured according to the conductivity which is sought after.

15 Claims, 1 Drawing Sheet

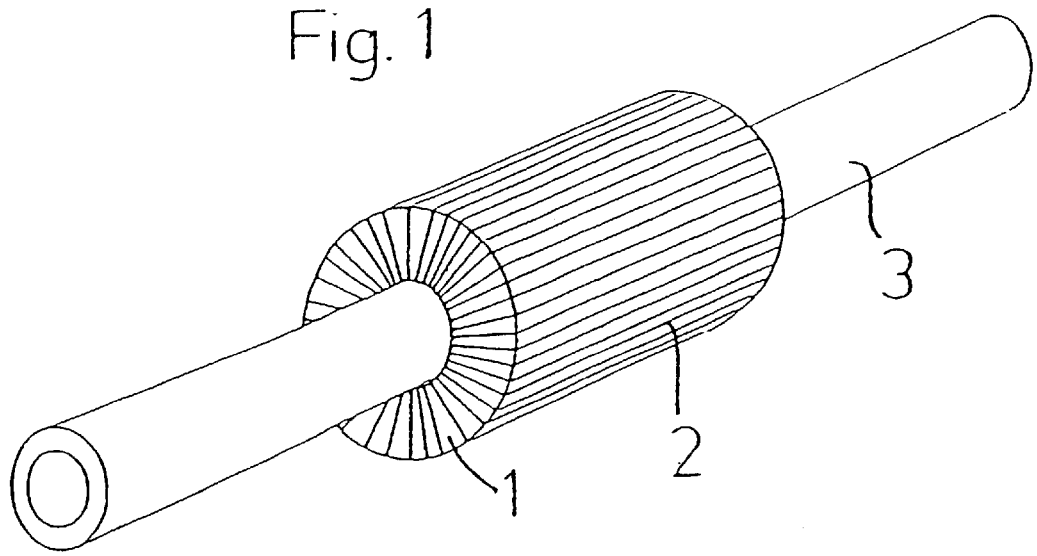
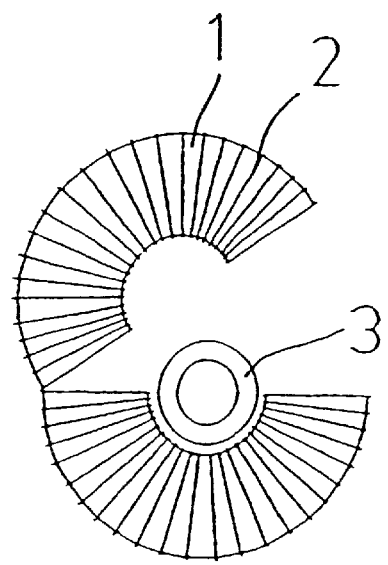

DEVICE AND METHOD FOR CARRYING OUT A CONTACTLESS MEASUREMENT OF THE CONDUCTIVITY OF A LIQUID SITUATED IN A FLOW CHANNEL

The present invention relates to a device and a method of contact-free measurement of the conductivity of a liquid in a flow channel and the use of said device and said method.

In many areas, such as dialysis, the conductivity of a liquid is used as an important measure of its composition. A standard method is to perform the measurement by using electrodes through which a current passes, but this is not suitable for measurements on disposable items such as tubing, because no electrodes can be incorporated into the disposable items for reasons of cost.

German Patent 37 18 111 C2 describes a device for contact-free (electrodeless) measurement of the conductivity of a liquid in a flow channel. A current flow is induced in the liquid by one coil, and the amperage is measured by another coil. This device is costly to manufacture and complicated to handle.

Thus, the object of the present invention is to create a device and a method of contact-free measurement of the conductivity of a liquid in a flow channel which is simple to handle and as inexpensive as possible.

This object is achieved according to the present invention by the fact that precisely one toroidal coil is arranged around the flow channel and can be connected to an electric analyzer circuit.

The present invention is based on the idea that a magnetic field that is variable over time is generated by a toroidal coil, its field lines forming concentric circles (at least ideally) running inside the toroidal coil. An electric field that is variable over time is generated due to the magnetic field that is variable over time inside the toroidal coil, with the field vector running in axial direction through the torus and thus running through the liquid channel arranged in the toroidal ring.

This electric field which changes polarity with the frequency of the coil current causes the ions in the liquid to move, which is equivalent to an alternating current axially through the liquid. Thus, the current is generated in the liquid by the same method as described in German Patent 37 18 111 C2. However, the power loss of the measurement arrangement caused by the current flow in the liquid and the ohmic resistance of the liquid is measured with the present invention instead of measuring the amperage of the current flowing through the liquid.

It has been found that with a suitable choice of the analyzer circuit and the coil as well as the liquid channel, the design of the ends of the liquid channel (valves, etc.) and the environment have only a negligible effect on the stability of the measurement signal.

No special design of the liquid channel is necessary. The liquid channel should advantageously have no elements such as valves that affect the liquid guidance and change over time for a length of several times 10 cm.

One embodiment of this device consists of the fact that the toroidal coil has a coil form wound with wire.

It is advantageous that the wire winding of the toroidal coil form a single layer.

It is also expedient that the coil form be made of a nonmagnetic material.

A refinement of the present invention consists of the fact that the toroidal coil is divided in axial direction.

It is also advantageous that the toroidal coil is to be opened for insertion of a flow channel.

In this way it is possible to introduce the flow channel, e.g., a tube, into the toroidal coil. The toroidal coil can also be placed around the edge of a disposable item (e.g., a cassette) to surround a liquid channel therein.

It is advantageous for at least one hinge to be provided for opening the toroidal coil.

Another embodiment of the present invention consists in being able to open the toroidal coil by a translational movement for inserting the flow channel.

The translational movement may be in the axial or radial direction.

A refinement of the present invention consists of the fact that the toroidal coil is connected to a capacitor to form an oscillating circuit.

One embodiment of the present invention provides for the analyzer circuit to have means for determining the damping of the oscillating circuit.

According to the present invention, it is provided that the analyzer circuit has means for determining the quality of the toroidal coil.

The conductivity is measured here by measuring the quality of the coil or measuring the damping of the sympathetic vibration in an oscillating circuit. In both cases, the coil is connected to a capacitor to form an oscillating circuit having a resonant frequency in the MHz range. The conductivity of the medium in the coil can be determined by measuring the oscillation amplitude on the coil and its change. A quality measurement can also be used; the ratio of the reactance to the active resistance of the arrangement in resonance is determined with it.

The present invention also concerns a method of contact-free measurement of the conductivity of a liquid in a flow channel having the following steps:

arranging a toroidal coil around a flow channel, with an analyzer circuit being connected to the toroidal coil, measuring electric quantities of the analyzer circuit, calculating the conductivity from the measured electric quantities of the analyzer circuit.

The change in electric quantities (quality of the toroidal coil, damping of the oscillation of an oscillating circuit) is thus measured in the area of the analyzer circuit and the conductivity is determined on the basis of these measured quantities. It would of course also be conceivable to perform the measurement of the electric quantities directly in the area of the toroidal coil and only perform the analysis in the analyzer circuit.

Finally, the use of the device according to the present invention or the method according to the present invention for measuring the conductivity of dialysis liquids is also within the scope of the present invention.

The present invention entails essentially the following advantages:

A simple measurement of conductivity on disposable items is also possible. The term "measurement" here is understood to refer not only to the absolute determination of the conductivity on the basis of a calibration curve but also to statements regarding the relative conductivity of the liquid.

No specific disposable items are necessary, because the toroidal coil can be arranged around normal tubes. When using disposable cassettes, only a liquid channel must be placed in the margin area of the cassette in order for the toroidal coil to be able to surround the liquid channel.

The device has only one coil, so the design is simpler and less expensive.

Handling is as simple as possible due to the fact that the coil is simply placed around the liquid channel.

A definite measurement effect is achieved; it is much greater than with a capacitive measurement and it can be analyzed by a relatively simple electronic circuit.

One embodiment of the present invention is described below on the basis of drawings, which show:

FIG. 1 a perspective view of a closed device according to the present invention, arranged around a liquid channel;

FIG. 2 a sectional diagram of an opened device according to the present invention with a liquid channel introduced into it.

As shown in FIG. 1, the device consists of a coil form 1 which is made of a nonmagnetic material (such as plastic). A single-layer coil winding 2 made of wire is applied to this coil form 1. Coil form 1 is divided axially (FIG. 2), and the two equally large halves can be opened, e.g. by a hinge. Opening the coil makes it possible to insert a liquid channel 3, e.g., a tube, into the device.

The toroidal coil is connected to a capacitor to form an oscillating circuit having a resonant frequency in the MHz range. With suitable dimensioning of the toroidal coil and suitable excitation of the oscillating circuit, changes in the voltage amplitude on the toroidal coil of approx. 2 Vss are achieved with a change in the conductivity of the liquid from approx. 7 mS/cm to approx. 17 mS/cm, i.e., in the physiologically relevant conductivity range.

This change in amplitude is analyzed by an analyzer circuit.

What is claimed is:

1. A device for contact-free measurement of the conductivity of a liquid in a flow channel, comprising:

only one toroidal coil, wherein the toroidal coil is adapted to be arranged around the flow channel; and an analyzer circuit connected to the toroidal coil;

wherein neither the toroidal coil nor the analyzer circuit contacts the liquid in the flow channel.

2. The device according to claim 1, wherein the toroidal coil further comprises a coil form and a wire winding wrapped on the coil form.

3. The device according to claim 2, wherein the wire winding of the toroidal coil is a single layer wire.

4. The device according to claim 2, wherein the coil form is made of a nonmagnetic material.

5. The device according to claim 1, wherein the toroidal coil is divided along an axial direction.

6. The device according to claim 5, wherein the divided toroidal coil is adapted to open for allowing insertion of a flow channel within the toroidal coil.

7. The device according to claim 5, further comprising at least one hinge connecting divided portions of the toroidal coil.

8. The device according to claim 1, wherein the toroidal coil is adapted for opening in response to a translational movement of the flow channel being inserted in the toroidal coil.

9. The device according to claim 1, further comprising a capacitor forming an oscillating circuit with the toroidal coil.

10. The device according to claim 9, wherein the analyzer circuit comprises means for determining a damping of the oscillating circuit.

11. The device according to claim 1, wherein the analyzer circuit has means for determining a quality of the toroidal coil.

12. The device according to claim 1, wherein the liquid is a dialysis liquid.

13. A method of performing contact-free conductivity measurement of a liquid in a flow channel, comprising the steps of:

disposing only one toroidal coil around the flow channel;

connecting an analyzer circuit to the toroidal coil;

measuring electric properties of the toroidal coil; and calculating the conductivity from the measured electric properties with the analyzer circuit;

wherein the method is performed without the use of an electrode.

14. The method according to claim 13, wherein the liquid is a dialysis liquid.

15. The method according to claim 13, wherein the analyzer circuit comprises a capacitor to form an oscillating circuit with the toroidal coil.

* * * * *